(12) United States Patent
Brown et al.

(10) Patent No.: US 12,110,547 B2
(45) Date of Patent: Oct. 8, 2024

(54) SELECTIVE SURFACE PATTERNING VIA NANOIMPRINTING

(71) Applicant: Illumina, Inc., San Diego, CA (US)

(72) Inventors: Andrew A. Brown, Cambridge (GB); Wayne N. George, Ilford (GB); Alexandre Richez, Cambridge (GB); M. Shane Bowen, Encinitas, CA (US)

(73) Assignee: Illumina, Inc., San Diego, CA (US)

( * ) Notice: Subject to any disclaimer, the term of this patent is extended or adjusted under 35 U.S.C. 154(b) by 1049 days.

(21) Appl. No.: 17/033,237

(22) Filed: Sep. 25, 2020

(65) Prior Publication Data

US 2021/0010080 A1 Jan. 14, 2021

Related U.S. Application Data

(62) Division of application No. 15/739,688, filed as application No. PCT/US2016/040951 on Jul. 5, 2016, now Pat. No. 10,808,282.

(60) Provisional application No. 62/189,662, filed on Jul. 7, 2015.

(51) Int. Cl.
| | |
|---|---|
| *G01N 33/53* | (2006.01) |
| *C12Q 1/6874* | (2018.01) |
| *G03F 7/00* | (2006.01) |
| *G03F 7/16* | (2006.01) |
| *B01L 3/00* | (2006.01) |
| *G01N 21/64* | (2006.01) |

(52) U.S. Cl.
CPC ......... *C12Q 1/6874* (2013.01); *G03F 7/0002* (2013.01); *G03F 7/161* (2013.01); *B01L 3/5085* (2013.01); *B01L 2200/12* (2013.01); *B01L 2300/0819* (2013.01); *B01L 2300/0829* (2013.01); *B01L 2300/161* (2013.01); *G01N 21/645* (2013.01)

(58) Field of Classification Search
None
See application file for complete search history.

(56) References Cited

U.S. PATENT DOCUMENTS

| | | | |
|---|---|---|---|
| 5,130,238 A | 7/1992 | Malek et al. | |
| 5,455,166 A | 10/1995 | Walker | |
| 5,599,675 A | 2/1997 | Brenner | |
| 5,622,294 A | 4/1997 | Evans et al. | |
| 5,641,658 A | 6/1997 | Adams et al. | |
| 5,750,341 A | 5/1998 | Macevicz | |
| 6,210,891 B1 | 4/2001 | Nyren et al. | |

(Continued)

FOREIGN PATENT DOCUMENTS

| | | |
|---|---|---|
| CN | 1437715 | 8/2003 |
| CN | 101114120 | 1/2008 |

(Continued)

OTHER PUBLICATIONS

Bains, et al., "A novel method for nucleic acid sequence determination", J. Theor. Biol., 135(3). 1988, 303-307.

(Continued)

*Primary Examiner* — Paul S Hyun

(74) *Attorney, Agent, or Firm* — Dierker & Kavanaugh, P.C.

(57) ABSTRACT

Substrates comprising dual functional polymer layered surfaces and the preparation thereof by using UV nano-imprinting processes are disclosed. The substrates can be used as flow cells, nanofluidic or microfluidic devices for biological molecules analysis.

13 Claims, 2 Drawing Sheets

Specification includes a Sequence Listing.

(56) References Cited

U.S. PATENT DOCUMENTS

| | | |
|---|---|---|
| 6,214,587 B1 | 4/2001 | Dattagupta |
| 6,258,568 B1 | 7/2001 | Nyren |
| 6,274,320 B1 | 8/2001 | Rothberg et al. |
| 6,355,431 B1 | 3/2002 | Chee et al. |
| 6,890,741 B2 | 5/2005 | Fan et al. |
| 6,913,884 B2 | 7/2005 | Stuelpnagel et al. |
| 7,057,026 B2 | 6/2006 | Barnes et al. |
| 7,115,400 B1 | 10/2006 | Adessi et al. |
| 7,211,414 B2 | 5/2007 | Hardin et al. |
| 7,244,559 B2 | 7/2007 | Rothberg et al. |
| 7,315,019 B2 | 1/2008 | Turner et al. |
| 7,329,492 B2 | 2/2008 | Hardin et al. |
| 7,405,281 B2 | 7/2008 | Xu et al. |
| 7,582,420 B2 | 9/2009 | Oliphant et al. |
| 7,595,883 B1 | 9/2009 | El Gamal et al. |
| 9,012,022 B2 | 4/2015 | George et al. |
| 2002/0055100 A1 | 5/2002 | Kawashima et al. |
| 2004/0002090 A1 | 1/2004 | Mayer et al. |
| 2004/0096853 A1 | 5/2004 | Mayer |
| 2005/0053980 A1 | 3/2005 | Gunderson et al. |
| 2005/0064460 A1 | 3/2005 | Holliger et al. |
| 2005/0130173 A1 | 6/2005 | Leamon et al. |
| 2005/0181440 A1 | 8/2005 | Chee et al. |
| 2005/0191698 A1 | 9/2005 | Chee et al. |
| 2006/0024813 A1 | 2/2006 | Warthoe |
| 2007/0099208 A1 | 5/2007 | Drmanac et al. |
| 2007/0128624 A1 | 6/2007 | Gormley et al. |
| 2007/0190786 A1 | 8/2007 | Murao et al. |
| 2007/0289119 A1 | 12/2007 | Lee et al. |
| 2008/0009420 A1 | 1/2008 | Schroth et al. |
| 2008/0108082 A1 | 5/2008 | Rank et al. |
| 2008/0219615 A1 | 9/2008 | Cunningham |
| 2009/0026082 A1 | 1/2009 | Rothberg et al. |
| 2009/0127589 A1 | 5/2009 | Rothberg et al. |
| 2009/0186349 A1 | 7/2009 | Gunderson et al. |
| 2009/0323014 A1 | 12/2009 | Cunningham et al. |
| 2010/0111768 A1 | 5/2010 | Banerjee et al. |
| 2010/0137143 A1 | 6/2010 | Rothberg et al. |
| 2010/0282617 A1 | 11/2010 | Rothberg |
| 2010/0311613 A1 | 12/2010 | Almed et al. |
| 2011/0059865 A1 | 3/2011 | Smith et al. |
| 2011/0076353 A1 | 3/2011 | Shirai et al. |
| 2011/0172118 A1 | 7/2011 | Kain et al. |
| 2012/0270305 A1 | 10/2012 | Reed et al. |
| 2012/0316086 A1 | 12/2012 | Lin et al. |
| 2013/0116153 A1 | 5/2013 | Bowen et al. |
| 2014/0079923 A1 | 3/2014 | George et al. |
| 2014/0243224 A1 | 8/2014 | Barnard et al. |
| 2015/0005447 A1 | 1/2015 | Berti et al. |
| 2015/0037815 A1 | 2/2015 | Miller et al. |
| 2015/0111005 A1 | 4/2015 | Hosomi et al. |
| 2016/0122816 A1 | 5/2016 | Brown et al. |

FOREIGN PATENT DOCUMENTS

| | | |
|---|---|---|
| CN | 101627336 | 1/2010 |
| CN | 102508408 | 6/2012 |
| CN | 103594555 | 2/2014 |
| WO | WO 1989/10977 | 11/1989 |
| WO | WO 1991/006678 | 5/1991 |
| WO | WO 2004/018497 | 3/2004 |
| WO | WO 2005/010145 | 2/2005 |
| WO | WO 2007/123744 | 11/2007 |
| WO | WO 2012/058096 | 5/2012 |
| WO | WO 2015/095291 | 6/2015 |

OTHER PUBLICATIONS

Bentley, et al., "Accurate whole human genome sequencing using reversible terminator chemistry", Nature, vol. 456, 2008, 53-59.

Billiet et al. "Triazolinediones enable ultrafast and reversible click chemistry for the design of dynamic polymer systems", Nature Chemistry 6, 2014, 815-821.

Dean, et al., "Comprehensive human genome amplification using multiple displacement amplification", Proc. Natl. Acad, Sci. USA 99. 2002, 5261-5266.

Dressman, et al., "Transforming single DNA molecules into fluorescent magnetic particles for detection and enumeration of genetic variations", Proc. Natl. Acad. Sci. USA 100 (15), 2003, 8817-8822.

Drmanac, et al., "Accurate sequencing by hybridization for DNA diagnostics and individual genomics", Nature Biotechnology, 1996, 54-58.

Fodor, et al., "Light-Directed, Spatially Addressable Parallel Chemical Synthesis", Science, vol. 251, 1991,767-773.

Korlach et al., "Selective aluminum passivation for targeted immobilization of single DNA polymerase molecules in zero-mode waveguide nanostructures", PNAS, vol. 105, No. 4, 2008, 1176-1181.

Lage, et al., "Whole genome analysis of genetic alterations in small DNA samples using hyperbranched strand displacement amplification and array-CGH", Genome Res., 2003, 294-307.

Levene, et al., "Zero-Mode Waveguides for Single-Molecule Analysis at high concentrations", Science 299, 2003, 682-686.

Lizardi, "Mutation detection and single-molecule counting using isothermal rolling-circle amplification", Nature Genetics, vol. 19,1998, 225-232.

Lunoquist, et al., "Parallel confocal detection of single molecules in real time", Opt. Lett. 33(9), 2008, 1026-1028.

Ronaghi, M., et al., "A Sequencing Method Based on Real-Time Pyrophosphate", Science 281 (5375}, Jul. 17, 1998, 363-365.

Ronaghi, M., "Pyrosequencing sheds light on DNA sequencing", Genome Res, 11(1 }, 2001, 3-11.

Ronaghi, M., et al.. "Real-time DNA sequencing using detection of pyrophosphate release", Anal. Biochem. Nov. 1, 1996, 242 (1): 84-9.

Sapsford, et al. "Functionalizing Nanoparticles with Biological Molecules: Developing Chemistries that Facilitate Nanotechnology", Chem Rev. 113, 2003, 1904-2074.

Shendure, et al., "Accurate Multiplex Polony Sequencing of an Evolved Bacterial Genome", Science, Sep. 9, 2005, 1728-1732.

Walker et al., "A Chemiluminescent DNA Probe Test Based on Strand Displacement Amplification". Molecular Methods for Virus Detection, 1995, Academic Press Inc., Ch. 15, pp. 329-349.

Walker, et al., "Strand displacement amplification-an isothermal, in vitro DNA amplification technique", Nucleic Acids Res., 1992, 1691-1696.

Chen et al. "Photonic crystal enhanced microscopy for imaging of live cell adhesion", Analyst, 2013, 138: 5886-5894 (Year: 2013).

PCT/US2016/040951, "International Search Report and Written Opinion" mailed Dec. 23, 2016.

Jung et al., "Paper: Dual-Layer thermal nanoimprint lithography without dry etching", Journal of Micromechanics and Microengineering, Institute of Physics, vol. 22, No. 8, Jul. 4, 2012.

SELECTIVE SURFACE PATTERNING VIA NANOIMPRINTING

CROSS-REFERENCE TO RELATED APPLICATION

This application is a divisional of U.S. patent application Ser. No. 15/739,688, filed Dec. 22, 2017, which is itself a U.S. National Stage Application of and claims priority to International Patent Application S.N. PCT/US2016/040951, filed on Jul. 5, 2016, which itself claims priority to U.S. Provisional Application Ser. No. 62/189,662, filed on Jul. 7, 2015; each of which aforementioned applications is hereby incorporated by reference in its entirety.

FIELD

In general, the present application relates to the fields of nano-patterning processes and related substrates having micro- or nano-patterned surfaces. More specifically, the present application relates to substrates comprising dual-functional polymer layered surfaces with binary surface chemistry. Methods of preparing these substrates by using nano-imprinting lithography processes are also disclosed.

BACKGROUND

Nano-imprinting technology enables the economic and effective production of nanostructures. Standard nano-embossing lithography employs direct mechanical deformation of a resist material by a stamp having nanostructures, followed by an etching process to transfer the nanostructures from the stamp to the substrate.

Flow cells are devices that allow fluid flow through channels or wells within a substrate. Patterned flow cells that are useful in nucleic acid analysis methods include discrete wells of active surface within an inert interstitial region. The surface of the flow cell is normally fabricated using the following steps: (1) wells are initially etched into a uniform substrate; (2) the wells and the interstitial regions are functionalized with a silane and a polymer or hydrogel; (3) excess polymer or hydrogel covering the interstitial regions is removed via a polishing process; (4) the polymer or hydrogel in the wells is then grafted with single stranded primer DNA to provide a flow cell surface for the downstream sequencing applications. In this case, some of the polymer or hydrogel is wasted in the polishing step of the fabrication workflow. In addition, the surface energy of the interstitial regions largely depends on the starting substrate.

REFERENCE TO SEQUENCE LISTING

The Sequence Listing submitted via EFS-Web on Sep. 28, 2020 is hereby incorporated by reference in its entirety. The name of the file is ILI147BUS_IP-1364A-US_Sequence_Listing_ST25.txt, the size of the file is 966 bytes, and the date of creation of the file is May 18, 2018.

SUMMARY

Embodiments of the present disclosure provide an improved substrate surface fabrication process by eliminating the need for polishing within the fabrication workflow of a patterned flow cell. In some instances, the chemical functionality within the patterned wells of the flow cell can be specifically chosen to directly capture a primer DNA. This can eliminate the need for a silane and functionalized polymer/hydrogel deposition onto the surface to capture DNA. In addition, the chemical functionality of the interstitial area could be chosen such that the overall surface energy of the final patterned surface is compatible with the proposed application. For example, the patterned surface can be hydrophilic, for example, to allow integration with a sequencing by synthesis (SBS) system using standard fluidics; or hydrophobic, for example, to allow repulsion of particular reagents, or reversibly convertible between a hydrophobic and hydrophilic state, for example, to be used in an electrowetting technique.

Some embodiments described herein are directed to a substrate having a surface comprising a first polymer layer disposed on the surface to form a first region, wherein the first polymer layer comprises a first plurality of functional groups; and a second polymer layer disposed over at least a portion of the first polymer layer to form a second region, wherein the first polymer layer comprises an imprinted pattern of features; and the first plurality of functional groups provide reactive sites for covalent bonding of a functionalized molecule. In some embodiments, the second polymer layer comprises a second plurality of functional groups that differ from first plurality of the functional groups in the first polymer layer.

Some embodiments described herein are directed to methods for preparing a substrate, comprising: providing a substrate having a first region and a second region; applying a layer of a first photocurable polymer composition to the first region and the second region; applying a layer of a second photocurable polymer composition on top of the layer of the first photocurable polymer composition to completely cover the layer of the first photocurable polymer composition; contacting the layer of the second photocurable polymer composition with a template having a plurality of micro-scale or nano-scale patterns; applying pressure to the template or the substrate to transfer said micro-scale or nano-scale patterns to the layer of the first and the second photocurable polymer compositions; irradiating UV light to cure the layers of the first and the second photocurable polymer compositions such that the layers of the first and the second photocurable polymer compositions form a first polymer layer and a second polymer layer respectively; and separating the template from substrate; wherein at least a portion of the second polymer layer is perforated to expose the underlying first polymer layer.

Some embodiments described herein are directed to methods for preparing a substrate, comprising: providing a substrate having a first patterned polymer layer on a surface of the substrate; depositing a first photonic crystal material on the first patterned polymer layer such that the first photonic crystal material adopts the patterns in the first patterned polymer layer; and forming a second patterned polymer layer on top of the photonic crystal material. In some embodiments, the methods further include depositing a second photonic crystal material on the second patterned polymer layer such that the second photonic crystal material adopts the patterns in the second patterned polymer layer.

Some embodiments described herein are directed to a substrate prepared by the methods described herein.

Some embodiments described herein are directed to methods of detecting an analyte using a substrate described herein.

DETAILED DESCRIPTION OF THE EMBODIMENTS

Figure 1:
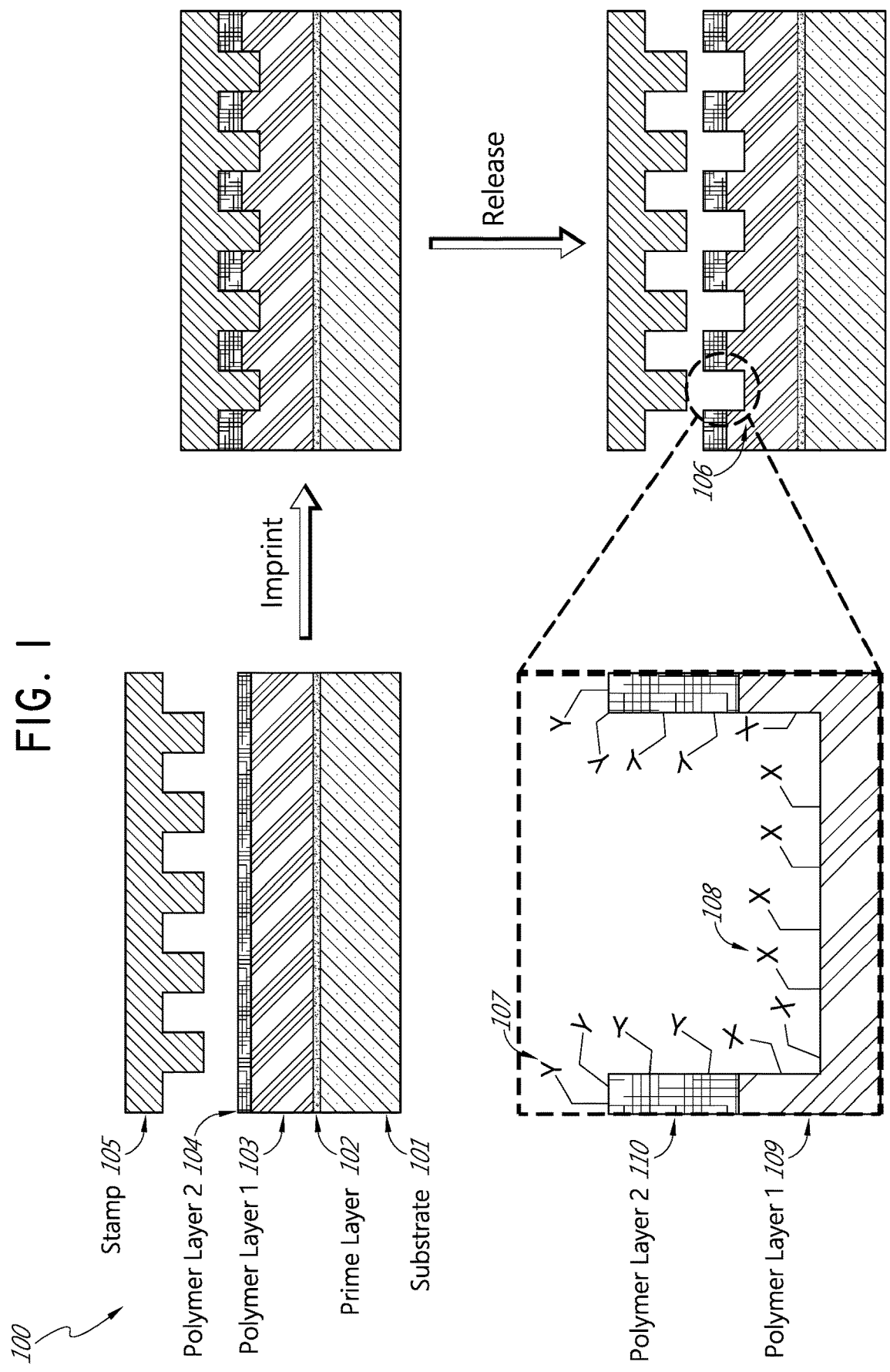
FIG. 1 illustrates an embodiment of the workflow process of preparing a dual polymer layer substrate using nano-imprinting lithography.

The standard nano-imprinting lithography process for preparing patterned flow cells can involve several steps, including: spin coating a layer of a polymer precursor formulation onto a primed wafer; soft baking the polymer precursor layer to drive out the solvent; imprinting the wafer and exposing to UV to initiate curing of the polymer precursor; and hard baking the wafer to complete the curing process and locking in the imprinted topography. In this standard setting, a single polymer precursor formulation is used, which results in an imprinted film of uniform chemical functionality throughout its volume. The surface of the well and interstitial area would have the same chemical functional groups at their surface.

In some embodiments the present application, two distinct polymer precursor formulations, each with tailored chemical functionality may be used in series to build up a dual-layer polymer coating ready for imprinting. The second (upper) layer may be thinner relative to the first (lower) layer. For example, the second (upper) layer may have a depth that is at most about 75%, about 70%, about 65%, about 60%, about 55%, about 50%, about 45%, about 40%, about 35%, about 30%, about 25%, about 20%, about 15%, about 10%, about 5% or less of the depth of the first (lower) layer, or a range defined by any of the two preceding values. Having a thinner upper layer can advantageously allow the upper layer polymer material to remain in place in the interstitial areas, but be perforated over the well surface area upon imprinting. In some instances, the pillars of the imprinting stamp would effectively pierce through the top layer polymer material such that the tips on the stamp pillars are only in contact with the lower layer polymer material.

In some embodiments, the second polymer precursor formulation would be deposited on a semi-cured first polymer precursor formulation layer to prevent the deposition of the second layer removing the first, or resulting in substantial intermixing of the two polymer precursor formulations.

In some embodiments, the two polymer precursor formulations would be designed such that they would bond together to form a covalently linked interface, yet retain orthogonal functionalities.

The use of dual layer nano imprint to form an imprinted surface with different chemical functionalities and for different downstream applications has been demonstrated by Jung et al. in the field of organic electronics. See Yunbum Jung and Xing Cheng, "Dual-layer thermal nanoimprint lithography without dry etching," 2012, *J. Micromech. Microeng.* 22(8), 085011.

The following detailed description is directed to certain specific embodiments of the present application. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment can be included in at least one embodiment of the invention. The appearances of the phrases "one embodiment," "an embodiment," or "in some embodiments" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The section headings used herein are for organizational purposes only and are not to be construed as limiting the subject matter described.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. As used in the specification and the appended claims, the singular forms "a," "an" and "the" include plural referents unless the context clearly dictates otherwise. The use of "or" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

As used herein, common organic abbreviations are defined as follows:
BCN Bicyclo[6.1.0]non-4-yne
NIL Nano-imprinting lithography
ssDNA Single stranded DNA
SBS Sequencing by synthesis
PAG Photoacid Generator
PAZAM poly(N-(5-azidoacetamidylpentyl) acrylamide-co-acrylamide) of any acrylamide to Azapa (N-(5-(2-azidoacetamido)pentyl)acrylamide) ratio
TAD 1,2,4-Triazoline-3,5-dione
° C. Temperature in degrees Centigrade
μm micrometer As used herein, the term "covalently attached" or "covalently bonded" refers to the forming of a chemical bonding that is characterized by the sharing of pairs of electrons between atoms. For example, a "covalently attached polymer coating," when used in reference to a substrate surface, refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via other means in addition to covalent attachment.

As used herein, the term "soft baking" or "soft bake" refers to a process of incubating or dehydrating a polymer or hydrogel formulation to drive out the solvent(s), where the duration of the process usually lasts from about 5 seconds to about 10 minutes at a temperature ranging from about 60° C. to about 130° C. Non-limiting examples of the devices that can be used for soft baking include hot plates.

As used herein, the term "hard baking" or "hard bake" refers to incubating or dehydrating a polymer formulation to drive out the solvent(s), where the duration of the process usually lasts from about 5 seconds to about 10 minutes at a temperature ranging from about 100° C. to about 300° C. Non-limiting examples of the devices that can be used for hard baking include hot plates.

As used herein, the term "feature" is intended to mean a discrete physical element or discrete physical trait of a substrate. A feature includes a location, position or site occupied, or available for occupancy on a substrate, or a distinguishable physical, structural or chemical trait of substrate. Therefore, a feature is a component of a substrate that provides physical or functional separability. A feature separates a biopolymer deposited at a first feature from a biopolymer deposited at a second feature. Examples of features include spots contained on a slide, chip or other planar substrate, a patterned substrate and separable chemical moieties or reactive groups.

A patterned substrate can include, for example, wells etched into a slide or chip. The pattern of the etchings and geometry of the wells can take on a variety of different shapes and sizes so long as such features are physically or functionally separable from each other.

As used herein, the term "polishing" is intended to mean mechanical or chemical treatment of a substrate, or a portion thereof, to remove a part of the substrate. Therefore, the term includes removing a coat of a substrate, including a coat of a layer of a substrate. Removal can be uniform or non-uniform. The term includes, for example, rubbing, chafing, smoothing, or otherwise treating a surface by the motion of applied pressure or other frictional forces as well as developing, finishing or refining the substrate to produce an altered surface of the substrate. The resultant surface is referred to herein as a "polished" surface. A direct polishing method can be used such that an abrasive surface contacts the surface to be polished or indirect polishing can be used such that a slurry or suspended aggregate is contacted with the surface in a lapping process. Specific examples of mechanical polishing include sanding, grinding or lapping. Chemical polishing methods can also be used such as treatment with acids such as hydrofluoric acid or bases such as sodium hydroxide. Other methods well known in the art that can remove a part of a substrate, including a part of a layer of a substrate, also are included within the meaning of the term as it is used herein.

As used herein, "functionalized molecule" refers to a molecule comprising reactive moieties that can be used to attach to the surface of a substrate or one or more biomolecules by way of a chemical reaction or molecular interaction. Such attachment may be via a covalent bond or through other bonding or interactive forces. In some embodiments the molecular interaction can be specific binding between a ligand and receptor, pairs of which include, but are not limited to, streptavidin and biotin, a nucleic acid and its complement, an antibody and ligand, and others known in the art. For example, a functionalized molecule can be a hydrogel comprising one or more functional groups that are capable of reacting with or binding to a biomolecule of interest. A non-limiting specific example is PAZAM comprising one or more azide functional groups, which can react with oligonucleotides comprising alkyne groups. In some instances, a functionalized molecule is attached to the surface of a substrate with reactive site(s) left for further attachment with biomolecules of interests. In some other instances, a functionalized molecule is attached to the surface of a substrate with no reactive site left. Alternative examples include polymers/hydrogels with tetrazine functional groups, which can react with oligonucleotides comprising strained rings (such as cyclic alkene or cyclic alkyne groups, for example norbornene and BCN functional groups), or polymers/hydrogels with epoxy or glycidyl groups, which can react with oligonucleotides comprising amino or protected amino groups. Additional examples are disclosed in U.S. Ser. No. 62/073,764, which is hereby incorporated by reference in its entirety.

As used herein, the term "photocurable polymer" refers to a polymer that is capable of undergoing a polymerization reaction when exposed to actinic radiation (such as UV radiation).

As used herein, the term "photonic crystal" refers to optical structures that affect the motion of photons. The photonic crystal materials in the substrates described herein are used for the purpose of light manipulation.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "cycloalkyl" means a fully saturated carbocyclic ring or ring system. Examples include cyclohexyl, cycloheptyl, cyclooctyl, etc.

As used herein, "cycloalkylene" means a fully saturated carbocyclic ring or ring system that is attached to the rest of the molecule via two points of attachment.

As used herein, "cycloalkenyl" or "cycloalkene" means a carbocyclic ring or ring system having at least one double bond, wherein no ring in the ring system is aromatic. An example is cyclooctene. Another example is norbornene or norbornenyl.

As used herein, "heterocycloalkenyl" or "heterocycloalkene" means a carbocyclic ring or ring system with at least one heteroatom in ring backbone, having at least one double bond, wherein no ring in the ring system is aromatic.

As used herein, "cycloalkynyl" or "cycloalkyne" means a carbocyclic ring or ring system having at least one triple bond, wherein no ring in the ring system is aromatic. An example is cyclooctyne. Another example is bicyclononyne.

As used herein, "heterocycloalkynyl" or "heterocycloalkyne" means a carbocyclic ring or ring system with at least one heteroatom in ring backbone, having at least one triple bond, wherein no ring in the ring system is aromatic.

An "amino" group refers to a "—NR$_A$R$_B$" group in which R$_A$ and R$_B$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 5-10 membered heterocyclyl, as defined herein. A non-limiting example includes free amino (i.e., —NH$_2$).

A "C-amido" group refers to a "—C(=O)NR$_A$R$_B$" group in which R$_A$ and R$_B$ are each independently selected from hydrogen, C$_{1-6}$ alkyl, C$_{2-6}$ alkenyl, C$_{2-6}$ alkynyl, C$_{3-7}$ carbocyclyl, C$_{6-11}$) aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, C$_{1-6}$ alkyl, C$_{2-6}$ alkenyl, C$_{2-6}$ alkynyl, C$_{3-7}$ carbocyclyl, C$_{6-11}$) aryl, 5-10 membered heteroaryl, and 5-10 membered heterocyclyl, as defined herein.

As used herein, the term "carboxylic acid" or "carboxyl" as used herein refers to —C(O)OH.

The term "hydrazine" or "hydrazinyl" as used herein refers to a —NHNH$_2$ group.

As used herein, the term "hydrazone" or "hydrazonyl" as used herein refers to

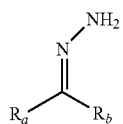

group in which R$_a$ and R$_b$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 5-10 membered heterocyclyl, as defined herein. A non-limiting example includes free amino (i.e., —NH$_2$).

The term "epoxy" as used herein refers to

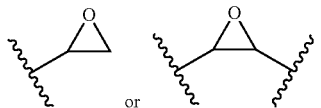

The term "glycidyl ether" as used herein refers to

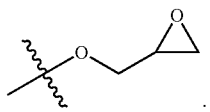 [SMILES: *OCC1CO1]

As used herein, the term "tetrazine" or "tetrazinyl" refers to six-membered heteroaryl group comprising four nitrogen atoms. Tetrazine can be optionally substituted.

As used herein, the term "tetrazole" or "tetrazolyl" refers to five membered heterocyclic group comprising four nitrogen atoms. Tetrazole can be optionally substituted.

An "nitrile oxide" as used herein, refers to a "RC≡N$^+$O$^-$" group in which R is selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, or 5-10 membered heterocyclyl, as defined herein. Non-limiting examples of preparing nitrile oxide include in situ generation from aldoximes by treatment with chloramide-T or through action of base on imidoyl chlorides [RC(Cl)=NOH].

An "nitrone" as used herein, refers to a "R$_A$R$_B$C=NR$_c$$^+$O$^-$" group in which R$_A$, R$_B$ and R$_c$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, or 5-10 membered heterocyclyl, as defined herein.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from C$_1$-C$_6$ alkyl, C$_1$-C$_6$ alkenyl, C$_1$-C$_6$ alkynyl, C$_1$-C$_6$ heteroalkyl, C$_3$-C$_7$ carbocyclyl (optionally substituted with halo, C$_1$-C$_6$ alkyl, C$_1$-C$_6$ alkoxy, C$_1$-C$_6$ haloalkyl, and C$_1$-C$_6$ haloalkoxy), C$_3$-C$_7$-carbocyclyl-C$_1$-C$_6$-alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), 5-10 membered heterocyclyl (optionally substituted with halo, C$_1$-C$_6$ alkyl, C$_1$-C$_6$ alkoxy, C$_1$-C$_6$ haloalkyl, and C$_1$-C$_6$ haloalkoxy), 5-10 membered heterocyclyl-C$_1$-C$_6$-alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), aryl (optionally substituted with halo, C$_1$-C$_6$ alkyl, C$_1$-C$_6$ alkoxy, C$_1$-C$_6$ haloalkyl, and C$_1$-C$_6$ haloalkoxy), aryl(C$_1$-C$_6$)alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), 5-10 membered heteroaryl (optionally substituted with halo, C$_1$-C$_6$ alkyl, C$_1$-C$_6$ alkoxy, C$_1$-C$_6$ haloalkyl, and C$_1$-C$_6$ haloalkoxy), 5-10 membered heteroaryl(C$_1$-C$_6$) alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), halo, cyano, hydroxy, C$_1$-C$_6$ alkoxy, C$_1$-C$_6$ alkoxy(C$_1$-C$_6$)alkyl (i.e., ether), aryloxy, sulfhydryl (mercapto), halo(C$_1$-C$_6$) alkyl (e.g., —CF$_3$), halo(C$_1$-C$_6$)alkoxy (e.g., —OCF$_3$), C$_1$-C$_6$ alkylthio, arylthio, amino, amino(C$_1$-C$_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present at the 2' position in ribose. The nitrogen containing heterocyclic base can be purine or pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but lacks any phosphate moieties at the 5' position. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

As used herein, the term "polynucleotide" refers to nucleic acids in general, including DNA (e.g. genomic DNA cDNA), RNA (e.g. mRNA), synthetic oligonucleotides and synthetic nucleic acid analogs. Polynucleotide may include both single-stranded DNA and double-stranded DNA. Polynucleotides may include natural or non-natural bases, or combinations thereof and natural or non-natural backbone linkages, e.g. phosphorothioates, PNA or 2'-O-methyl-RNA, or combinations thereof.

As used herein, the term "primer" is defined as a single strand DNA (ssDNA) molecule with a free 3' OH group and a modification at the 5' terminus to allow the coupling reactions. The primer length can be any number of bases long and can include a variety of non-natural nucleotides. In some embodiments, "SBS primers" are used as part of a sequencing by synthesis (SBS) reaction on a system such as the HiSeq®, MiSeq® or NextSeq® systems from Illumina (San Diego, CA). In these reactions, a set of amplification primers are typically bound to a glass surface. A set of target DNA molecules to be sequenced is hybridized to the bound primers and then amplified by a bridge amplification process. The sequencing reactions are carried out, and in embodiments of the invention, the amplification primers (and amplicons including primers extended during amplification steps to include copies of the target DNA) are then unbound from the glass surface so that the surface is reusable in future sequencing reactions. Thus, one or more of the steps of attaching amplification primers to the glass surface, hybridizing target DNA molecules to the primers, bridge amplification, sequencing the target DNA, and removing amplification primers and amplicons can be repeated. One or more repetition can be carried out. In some embodiments, the SBS primers can be the P5 or P7 primers in one embodiment, as detailed below. The P5 and P7 primers are used on the surface of commercial flow cells sold by Illumina Inc. for sequencing on the HiSeq®, MiSeq®, NextSeq® and Genome Analyzer® platforms. The primer sequences are described in US Pat. Pub. No. 2011/0059865 A1, which is incorporated herein by reference in its entirety.

The P5 and P7 primer sequences comprise the following:

```
The P5 and P7 primer sequences comprise the
following:
Paired end set:
P5: paired end 5' → 3'
                                        (SEQ ID NO: 1)
AATGATACGGCGACCACCGAGAUCTACAC P7: paired end 5' → 3'
                                        (SEQ ID NO: 2)
CAAGCAGAAGACGGCATACGAG*AT Single read set:
P5: single read: 5' → 3'
                                        (SEQ ID NO: 3)
AATGATACGGCGACCACCGA P7: single read 5' → 3'
                                        (SEQ ID NO: 4)
CAAGCAGAAGACGGCATACGA
```

Optionally, one or both of the P5 and P7 primers can include a poly T tail. The poly T tail is generally located at the 5' end of the above sequences, but in some cases can be located at the 3' end. The poly T sequence can include any number of T nucleotides, for example, from 2 to 20.

In some embodiments, the "SBS primer" is a "BCN primer" or a "BCN modified primer," which refers to a primer comprising covalently attached bicyclo[6.1.0]non-4-yne at the 5' terminus. Other non-limiting exemplary primers include a tetrazine terminated primer, a norbornene terminated primer, an azido terminated primer, an alkyne terminated primer, an amino terminated primer, an epoxy or glycidyl terminated primer, a thiophosphate terminated primer, and triazolinedione terminated primer.

As used herein, the term "percent surface remaining" can refer to the intensity measured using a TET QC to stain the P5/P7 surface primers. The P5 and P7 primers are used on the surface of commercial flow cells sold by Illumina Inc. for sequencing on the HiSeq, MiSeq, Genome Analyzer and NextSeq platforms. The primer sequences are described in U.S. Pat. Pub. No. 2011/0059865 A1, which is incorporated herein by reference. TET is a dye labeled oligonucleotide having complimentary sequence to the P5/P7 primers. TET can be hybridized to the P5/P7 primers on a surface; the excess TET can be washed away, and the attached dye concentration can be measured by fluorescence detection using a scanning instrument such as a Typhoon Scanner (General Electric).

The skilled artisan will recognize that some structures described herein may be resonance forms or tautomers of compounds that may be fairly represented by other chemical structures; the artisan recognizes that such structures may only represent a very small portion of a sample of such compound(s). Such compounds are considered within the scope of the structures depicted, though such resonance forms or tautomers are not represented herein.

Substrate Surface

Some embodiments described herein are directed to a surface of a substrate comprising a first region and a second region, wherein the first region comprises a first polymer layer, and the first polymer layer has a first plurality of functional groups, and wherein the first plurality of functional groups provide reactive sites for covalent bonding of a functionalized molecule. The substrate also may have a second region that includes the first polymer layer and a second polymer layer, wherein the second polymer layer is on top of, directly adjacent to, or adjacent to the first polymer layer. The second polymer layer may completely cover the underlying first polymer layer, and may optionally provide a second plurality of functional groups. It should also be realized that the second polymer layer may cover only a portion of the first polymer layer in some embodiments. In some embodiments the second polymer layer covers a substantial portion of the first polymer layer, wherein the substantial portion includes greater than about 50%, about 55%, about 60%, about 65%, about 70%, about 75%, about 80%, about 85%, about 90%, about 95%, or about 99% coverage of the first polymer layer, or a range defined by any of the two preceding values. In some embodiments, the first and the second polymer layers do not comprise silicon or silicon oxide.

In some embodiments, the first region is patterned.

In some embodiments, the first region comprises micro-scale or nano-scale patterns. In some such embodiments, the micro-scale or nano-scale patterns comprise channels, trenches, posts, wells, or combinations thereof. For example, the pattern can include a plurality of wells or other features that form an array. High density arrays are characterized as having features separated by less than about 15 µm. Medium density arrays have features separated by about 15 to about 30 µm, while low density arrays have sites separated by greater than about 30 µm. An array useful herein can have, for example, features that are separated by less than about 100 µm, about 50 µm, about 10 µm, about 5 µm, about 1 µm, or about 0.5 µm, or a range defined by any of the two preceding values.

In particular embodiments, features on a substrate can each have an area that is larger than about 100 nm², about 250 nm², about 500 nm², about 1 µm², about 2.5 µm², about 5 µm², about 10 µm², about 100 µm², or about 500 µm², or a range defined by any of the two preceding values. Alternatively or additionally, features can each have an area that is smaller than about 1 mm², about 500 µm², about 100 µm², about 25 µm², about 10 µm², about 5 µm², about 1 µm², about 500 nm², or about 100 nm², or a range defined by any of the two preceding values.

A substrate can include, or can be made by the methods set forth herein to include, a plurality of wells or other features that include at least about 10, about 100, about $1\times10^3$, about $1\times10^4$, about $1\times10^5$, about $1\times10^6$, about $1\times10^7$, about $1\times10^8$, about $1\times10^9$ or more features, or a range defined by any of the two preceding values. Alternatively or additionally, a substrate can include at most about $1\times10^9$, about $1\times10^8$, about $1\times10^7$, about $1\times10^6$, about $1\times10^5$, about $1\times10^4$, about $1\times10^3$, about 100, about 10 or fewer features, or a range defined by any of the two preceding values.

A pattern of features can be characterized in terms of average pitch. The pattern can be ordered such that the coefficient of variation around the average pitch is small or the pattern can be random in which case the coefficient of variation can be relatively large. In either case, the average pitch can be, for example, at least about 10 nm, about 0.1 µm, about 0.5 µm, about 1 µm, about 5 µm, about 10 µm, about 100 µm or more, or a range defined by any of the two preceding values. Alternatively or additionally, the average pitch can be, for example, at most about 100 µm, about 10 µm, about 5 µm, about 1 µm, about 0.5 µm, about 0.1 µm or less, or a range defined by any of the two preceding values.

In some embodiments, the second region is not patterned. In some embodiments, the second region is an interstitial space of the first region.

In some embodiments, the first region is hydrophilic. In some other embodiments, the first region is hydrophobic. The second region can, in turn be hydrophilic or hydrophobic. In particular cases, the first and second regions have opposite character with regard to hydrophobicity and hydrophilicity.

In some embodiments, the first plurality of functional groups of the first polymer layer are selected from $C_{8-14}$ cycloalkenes, 8 to 14 membered heterocycloalkenes, $C_{8-14}$ cycloalkynes, 8 to 14 membered heterocycloalkynes, alkynyl, vinyl, halo, azido, amino, amido, epoxy, glycidyl, carboxyl, hydrazonyl, hydrazinyl, hydroxy, tetrazolyl, tetrazinyl, nitrile oxide, nitrene, nitrone, or thiol, or optionally substituted variants and combinations thereof. In some such embodiments, the first plurality of functional groups are selected from $C_{8-14}$ cycloalkenes, $C_{8-14}$ cycloalkynes, alkynyl, vinyl, halo, azido, amino, amido, epoxy, glycidyl, carboxyl, hydrazonyl, hydrazinyl, hydroxy, tetrazolyl, tetrazinyl, nitrile oxide, nitrene, nitrone, or thiol, or optionally substituted variants and combinations thereof. In some such embodiments, the first plurality of functional groups are selected from halo, azido, alkynyl, carboxyl, epoxy, glycidyl, norbornene, or amino, or optionally substituted variants and combinations thereof.

In some embodiments, the second polymer layer comprises a second plurality of functional groups that differ from the first plurality of functional groups in the first polymer layer.

In some embodiments, the thickness of the first polymer layer is greater than that of the second polymer layer.

In some embodiments, the surface of the substrate further comprises a functionalized molecule, wherein the functionalized molecule includes a polymer, a hydrogel, an amino acid, a peptide, a nucleoside, a nucleotide, a polynucleotide, a sugar, a protein, or combinations thereof covalently attached to the surface through reaction with the first plurality of functional groups. Exemplary hydrogels that can be used in the methods and compositions set forth herein include, but are not limited to, those having a colloidal structure, such as agarose; polymer mesh structure, such as gelatin; or cross-linked polymer structure, such as polyacrylamide, SFA (see, for example, U.S. Pat. App. Pub. No. 2011/0059865 A1, which is incorporated herein by reference) or poly(N-(5-azidoacetamidylpentyl)acrylamide-co-acrylamide) (PAZAM, see for example, U.S. Pat. App. Publ. Nos. 2014/0079923 A1, or 2015/0005447 A1, each of which is incorporated herein by reference).

In some embodiments, the functionalized molecule comprises PAZAM. In some such embodiments, the functionalized molecule further comprises oligonucleotides covalently bonded to PAZAM.

PAZAM

PAZAM is represented by the following structures:

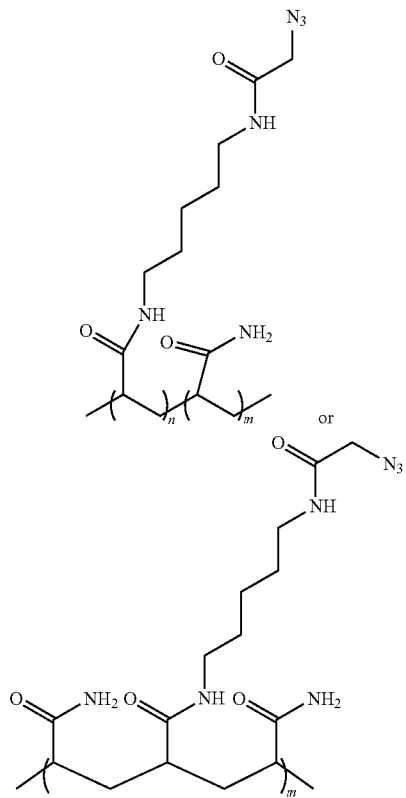

wherein n is an integer in the range of 1-20,000, and m is an integer in the range of 1-100,000. In some embodiments, PAZAM is a linear polymer. In some other embodiments, PAZAM is a lightly cross-linked polymer.

PAZAM can be functionalized or modified for use in a composition or method set forth herein. Non-limiting examples of the functionalized polymers that can be used, for example, by being attached to the surface of a substrate, are disclosed in U.S. Pat. No. 9,012,022, which is hereby incorporated by reference in its entirety.

In some embodiments, the substrate further comprises a layer of photonic crystals deposited between the first and the second polymer layers. In some such embodiments, the photonic crystal comprises a material having high refractive index and low adsorption characteristics. In one embodiment, the photonic crystal material comprises $Ta_2O_5$.

Methods of Manufacturing

Some embodiments described herein are directed to methods for preparing a substrate, and include providing a substrate having a first region and a second region; applying or depositing a layer of a first photocurable polymer composition to the first region and the second region; applying or depositing a layer of a second photocurable polymer composition on top of the layer of the first photocurable polymer composition to completely cover the layer of the first photocurable polymer composition; contacting the layer of the second photocurable polymer composition with a template having a plurality of micro-scale or nano-scale patterns; applying pressure to the template or the substrate to transfer said micro-scale or nano-scale patterns to the layer of the first and the second photocurable polymer compositions; irradiating UV light to cure the layers of the first and the second photocurable polymer compositions such that the layers of the first and the second photocurable polymer compositions form a first polymer layer and a second polymer layer respectively; and separating the template from substrate; wherein at least a portion of the second polymer layer is perforated or penetrated to expose the underlying first polymer layer. It should also be realized that the second photocurable polymer compositions may cover only a portion of the first photocurable polymer compositions in some embodiments, resulting in the second polymer layer covering a substantial portion of the first polymer layer after UV curing, wherein the substantial portion includes greater than about 50%, about 55%, about 60%, about 65%, about 70%, about 75%, about 80%, about 85%, about 90%, about 95%, or about 99% coverage of the first polymer layer, or a range defined by any of the two preceding values. In some other embodiments, thermal curable polymer compositions may be used in place of the photocurable polymer compositions.

In some embodiments, the thickness of the layer of the first photocurable polymer composition is greater than that of the second photocurable polymer composition.

In some embodiments, the second polymer layer is completely perforated or penetrated to expose the underlying first polymer layer.

In some embodiments, the methods further include semi-curing the layer of the first photocurable polymer composition prior to applying the layer of the second photocurable polymer composition. The term "semi-curing" as used herein, refers to exposing a photocurable polymer composition to UV and/or heat for a limited period of time to produce a layer which is incompletely polymerized. In some embodiments, the percentage completion of polymerization is greater than about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, or a range defined by any of the two preceding values. The purposes of the semi-curing step include, but not limited to, preventing physical mixing between the first photocurable polymer composition and the second photocurable polymer composition, and preventing the removal of the layer of the first photocurable polymer composition when the layer of the second photocurable polymer composition is deposited on top.

In some embodiments, the methods further include drying the layers of the first and second photocurable polymer compositions prior to contacting with the template.

In some embodiments, the methods further include drying the first polymer and the second polymer layers after irradiating UV light.

In some embodiments, the micro-scale or nano-scale patterns comprise channels, trenches, posts, wells, or combinations thereof.

In some embodiments, the first polymer layer comprises a first plurality of functional groups. In some embodiments, the second polymer layer comprises a second plurality of functional groups that differ from the first plurality of functional groups.

In some embodiments, the first plurality of functional groups of the first polymer layer are selected from $C_{8-14}$ cycloalkenes, 8 to 14 membered heterocycloalkenes, $C_{8-14}$ cycloalkynes, 8 to 14 membered heterocycloalkynes, alkynyl, vinyl, halo, azido, amino, amido, epoxy, glycidyl, carboxyl, hydrazonyl, hydrazinyl, hydroxy, tetrazolyl, tetrazinyl, nitrile oxide, nitrene, nitrone, or thiol, or optionally substituted variants and combinations thereof. In some such embodiments, the first plurality of functional groups are selected from halo, azido, alkynyl, carboxyl, epoxy, glycidyl, norbornene, or amino, or optionally substituted variants and combinations thereof.

In some embodiments, the surface of the substrate also has a functionalized molecule comprising a polymer, a hydrogel, an amino acid, a peptide, a nucleoside, a nucleotide, a polynucleotide, a sugar, a protein, or combinations thereof covalently attached to the surface. In some embodiments, the functionalized molecule is covalently attached to the surface of the substrate through reaction with the first plurality of functional groups. In some further embodiments, the functionalized molecule comprises poly(N-(5-azidoacetamidylpentyl)acrylamide-co-acrylamide) (PAZAM) or a derivative thereof.

FIG. 1 illustrates an embodiment of workflow of preparing a dual-layer substrate using the nano-imprinting lithography method described herein. The system 100 comprises a substrate 101, a prime layer 102, a layer of a first photocurable polymer composition 103, a layer of a second photocurable polymer composition 104, and a stamp 105. The layer of the second photocurable polymer composition 104 is on top, and in direct contact with, the layer of the first photocurable polymer composition 103. In addition, the thickness of layer 104 is thinner than the thickness of layer 103 in this embodiment. After soft baking the photocurable polymer precursor layers to remove excess solvent, stamp 105 is pressed against the layer of the second photocurable polymer composition 104 to create an imprint on the second photocurable polymer composition 104 and the layer of the first photocurable polymer composition 103 such that layer 104 is perforated by the teeth of the stamp 105. After UV curing, stamp 105 is released.

Pattern 106 from stamp 105 is thereby transferred to the substrate, resulting in a patterned substrate with two polymer layers: polymer layer 109 is formed from the first photocurable polymer composition 103 and includes chemical functionality 108. Polymer layer 110 is formed from the second photocurable polymer composition 104 and includes chemical functionality 107. The substrate may be subject to further heat curing to complete the UV cure and locking the imprinted topography. In some embodiments, the heat curing may be performed at a temperature ranging from about 60° C. to about 300° C.

In some embodiments, the functional groups (X) in polymer layer 109 are within the well surface of the flow cell and may be available for further functionalization to capture single stranded DNA (ssDNA), if required, for DNA sequencing procedures. This functionalization process may or may not include the selective capture of a polymeric support (e.g. PAZAM) to the flow cell well surface. The functional groups (Y) in polymer layer 110 are within the interstitial area in contact with the flow cell channel lumen. Functional groups Y could also act as an anchor point for further modification, using chemistry which is orthogonal to that used in polymer layer 109. For example, polymer layer 110 or modifications thereof, will act as a barrier, or passivation layer to the functional groups present in polymer layer 109 within the interstitial region.

Photocurable Polymer Compositions

Various photocurable polymer compositions may be used in the present application.

In some embodiments, a photocurable polymer precursor composition containing a silsesquioxane cage (also known as a "POSS" unit as illustrated in the chemical structure below) may be used:

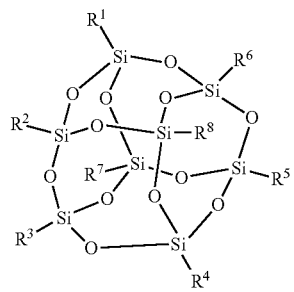

These monomeric units typically have eight arms of functional group $R^1$ through $R^8$. In some embodiments, $R^1$-$R^8$ comprise moieties selected from azido, epoxy, glycidyl, glycidyl ether, urethane, norbornene, acrylic acid, maleic acid, acrylate, vinyl, ethynyl, or combinations thereof.

In some embodiments, functional groups $R^1$-$R^8$ are the same. In some other embodiments, $R^1$-$R^8$ are not the same. In one embodiment, each of $R^1$-$R^8$ is terminated in epoxy groups which allow the polymer precursor to polymerize into a crosslinked matrix upon initiation using ultraviolet (UV) light.

In some embodiments, a molecule containing both epoxy groups and at least one other orthogonal functional group (X or Y) is added to the photocurable polymer composition. The epoxy group allows the additive to be covalently crosslinked into the polymer matrix. The X or Y group is the functionality of interest which modifies the properties of the cured polymer layer. A general schematic for the polymer chemistry is shown below in Scheme 1:

Scheme 1 Polymerization of photocurable polymer composition to give a crosslinked polymer film containing a functional group of interest (X or Y).

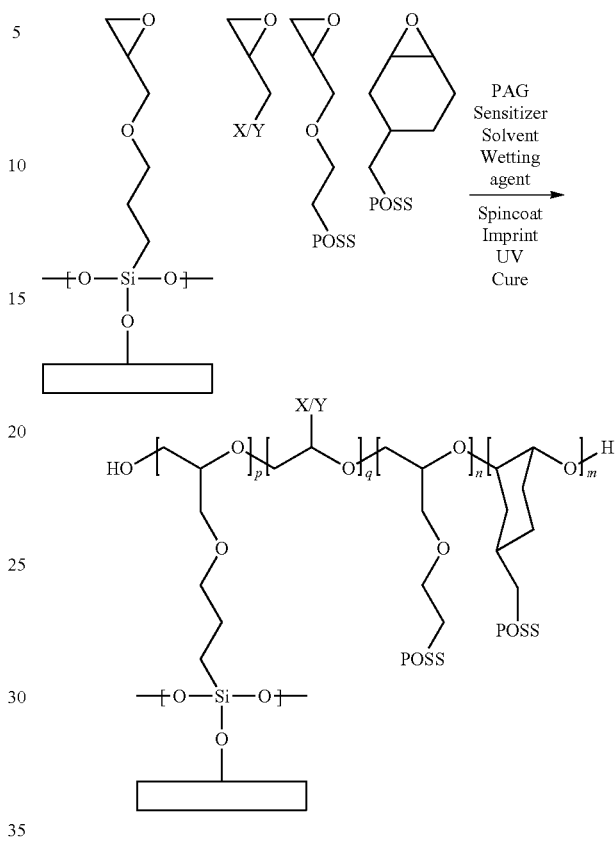

In some cases, silane is only necessary for substrates which need an adhesion layer. The ratio of monomers within the final polymer (p:q:n:m) depends on the stoichiometry of the monomers in the initial polymer formulation mix.

The silane molecule contains an epoxy unit can be incorporated covalently into the first and lower polymer layer contacting the substrate. For the second and upper polymer layer which is deposited on the semi-cured first layer, no such silane molecule is required. The first polymer layer will naturally propagate polymerization into the monomeric units of the second polymer layer covalently linking them together.

In some embodiments of the methods described herein, a primed substrate is spin coated with a first epoxy based NIL photocurable polymer composition, containing the additive epihalohydrin of the structure

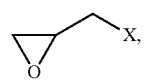

wherein X is halogen. In one particular embodiment, the additive is epibromohydrin

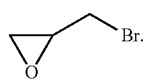

The second photocurable polymer composition is an epoxy based NIL polymer formulation containing the additive glycidol of the structure

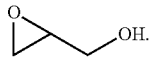

After the imprinting process, the epibromohydrin containing first and lower polymer layer will contain alkylene bromide groups in the contacting phase within the walls of the substrate wells. The glycidol containing second and upper polymer layer covering the interstitial areas should mask any alkylene bromide groups in the interstitial regions from the contacting phase, and also provide a hydrophilic interstitial surface. As used herein, the contact phase refers to the outer layer of the substrate which comes into contact with a fluid pumped over the surface. The fluid may include SBS reagents (such as template DNA or primers solutions, polynucleotide polymerase solutions), analyte fluid, or storage buffers, etc.

The alkylene bromide groups in the substrate well walls act as anchor points for further spatially selective functionalization. For example, the alkylene bromide groups may be reacted with sodium azide to create an azide coated well surface. This azide surface could then be used directly to capture alkyne terminated oligos using copper catalyzed click chemistry as outlined in Scheme 2, or bicyclo[6.1.0] non-4-yne (BCN) terminated oligos using strain-promoted catalyst-free click chemistry. Detailed disclosure on strain-promoted catalyst free ring opening reactions for SBS applications is disclosed in U.S. Patent Publication 2015/0005447 A1, which is hereby incorporated by reference in its entirety.

Scheme 2 Conversion of alkylene bromide containing cured polymer surface to azide with subsequent oligo coupling using alkyne/oligo click chemistry.

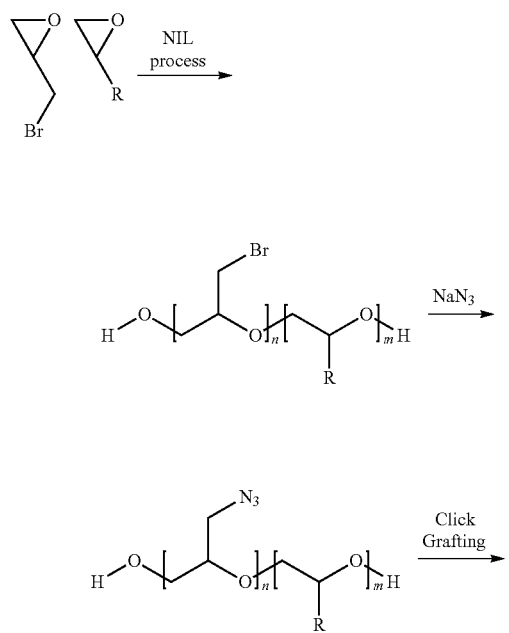

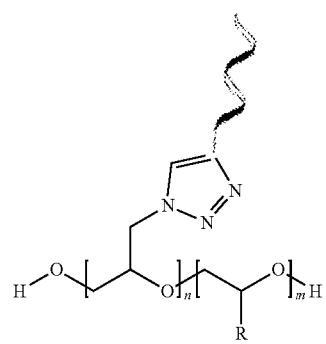

In Scheme 2, "R" represents the POSS and silane units as shown in Scheme 1. The azide conversion and grafting will take place after the layer of the second photocurable polymer composition is deposited and the dual-layer imprinting process completed to ensure the chemical modification is isolated to the well surface of the substrate.

Alternatively, sodium azide can be replaced with a norbornene functionalized amine or dibenzocyclooctynes (DIBO) functionalized amine to provide strained ring moiety to the polymer, which can subsequently undergoing catalyst-free ring strain promoted click reaction with a tetrazine functionalized oligos to graft the primers to surface. A detailed disclosure on chemical functionalization of the biological molecules of interest is summarized by Sapsford et al., *Chem. Rev.* 2003, 113, 1904-2074.

One example of preparing a second photocurable polymer composition, which will become the interstitial polymer layer, is outlined in Scheme 3.

Scheme 3

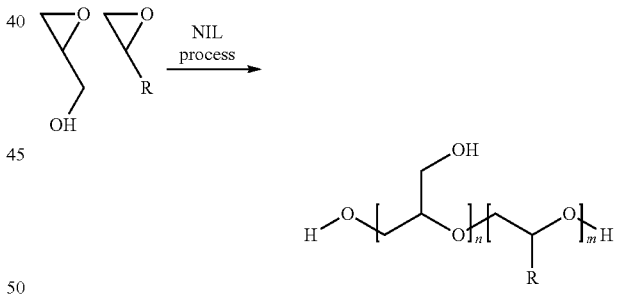

Addition of glycidol to the second photocurable polymer composition would yield a polymer surface with numerous hydroxyl groups (R represents the POSS and silane units as shown in Scheme 1).

In another embodiment of the methods described herein, the alkylene bromide groups may be reacted with 5-norbornene-2-methanamine, to create a norbornene coated well surface. The azide containing polymer, PAZAM, may then be coupled selectively to this norbornene surface localized in the wells, and further be grafted with alkyne terminated oligos as exemplified in Scheme 4. BCN terminated oligos may also be used in lieu of the alkyne terminated oligos via a catalyst-free strain promote cycloaddition reaction.

Scheme 4 Conversion of alkylene bromide well surface to a norbornene surface ready for PAZAM capture and subsequent grafting.

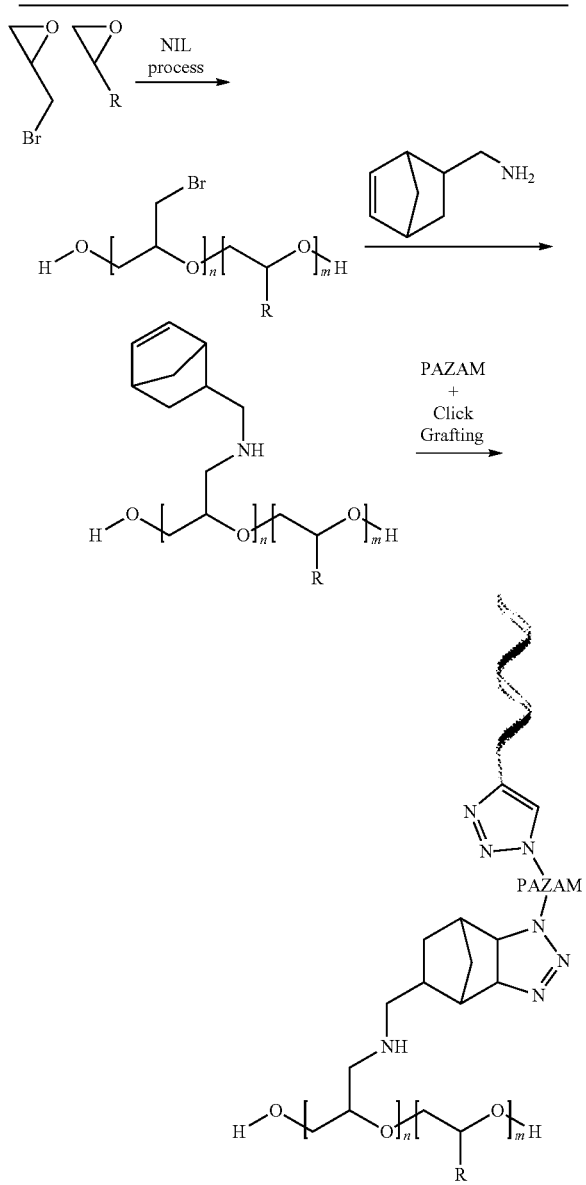

With an inert second polymer layer covering the interstitial regions of the substrate, the PAZAM coupling and grafting is localized to the wells of the substrate (R represents the POSS and silane units as shown in Scheme 1). In addition, because there are no norbornene moieties in the interstitial area, the excess PAZAM can be removed by mild solvent washing, rather than aggressive polishing. Both approaches result in a patterned surface of wells where the well surface is selectively modified into a state ready for sequencing, while the interstitial area remains inert.

Alternatively, tetrazine terminated oligos may be grafted directly to the polymer by reacting with the norbornene moiety, thereby eliminating the PAZAM coupling step.

The choice of functionality within each photocurable polymer composition is dependent on the choice of additive used. There are a number of small molecules, polymers and silsesquioxanes that can be used to achieve this goal. In addition, these additives may be used in single layer nanoimprint lithography to impart new chemical functionalities into the cured polymer layer, or change the polymer layer properties, for example, surface energy, although using them in conjunction with a dual layer NIL process would greatly simplify workflows.

Non-limiting examples of the additives that may be used in the photocurable polymer composition of the present application include: epibromohydrin, glycidol, glycidyl propargyl ether, methyl-5-norbornene-2,3-dicarboxylic anhydride, 3-azido-1-propanol, tert-butyl N-(2-oxiranylmethyl)carbamate, propiolic acid, 11-azido-3,6,9-trioxaundecan-1-amine, cis-epoxysuccinic acid, 5-norbornene-2-methylamine, 4-(2-oxiranylmethyl)morpholine, glycidyltrimethylammonium chloride, phosphomycin disodium salt, poly glycidyl methacrylate, poly(propylene glycol) diglycidyl ether, poly(ethylene glycol) diglycidyl ether, poly[dimethylsiloxane-co-(2-(3,4-epoxycyclohexyl)ethyl)methylsiloxane], poly[(propylmethacryl-heptaisobutyl-PSS)-co-hydroxyethyl methacrylate], poly[(propylmethacryl-heptaisobutyl-PSS)-co-(t-butyl methacrylate)], [(5-bicyclo[2.2.1]hept-2-enyl)ethyl]trimethoxysilane, trans-cyclohexanediolisobutyl POSS, aminopropyl isobutyl POSS, octa tetramethylammonium POSS, poly ethylene glycol POSS, octa dimethylsilane POSS, octa ammonium POSS, octa maleamic acid POSS, trisnorbornenylisobutyl POSS, fumed silica, surfactants, or combinations and derivatives thereof.

Methods of Manufacturing Substrates Containing Photonic Crystals

Some embodiments described herein are directed to methods for preparing a substrate, comprising: providing a substrate having a first patterned polymer layer on a surface of the substrate; depositing a first photonic crystal material on the first patterned polymer layer such that the first photonic crystal material adopts the patterns in the first patterned polymer layer; and forming a second patterned polymer layer on top of the photonic crystal material.

In some embodiments, the methods further include depositing a second photonic crystal material on the second patterned polymer layer such that the second photonic crystal material adopts the patterns in the second patterned polymer layer.

The first and the second patterned polymer layers may be independently prepared by various techniques known to one of skilled in the art. In some embodiments, the first and the second patterned polymer layers are prepared by mechanical embossing, nanoimprint lithography, or resist-free nanoimprint lithography. In one particular embodiment, the patterned polymer layers are prepared by resist-free nanoimprint lithography. In some embodiments, the patterns in the first polymer layer are substantially the same as the patterns in the second polymer layer. In some other embodiments, the patterns in the first polymer layer are different from the patterns in the second polymer layer; for example, they are complimentary to the patterns in the second polymer layer.

In some embodiments, the first photonic crystal material is deposited onto the first polymer layer by sputter deposition. As used herein, "sputter deposition" refers to a physical vapor deposition (PVD) method of thin film/coating deposition by sputtering. This process involves ejecting material from a source onto a substrate. In particular, the sputter deposition used in the methods described herein forms a thin layer of a photonic crystal coating on the surface of the substrate. In some embodiments, the photonic crystal materials used in sputter deposition include metals and metal oxides with high refractive index and low adsorption characteristics. In one particular embodiment, the photonic crystal material includes tantalum pentoxide (also known as tantalum oxide, $Ta_2O_5$). When the underlying surface is patterned, the photonic crystal layer/coating will also adopt the patterns in the underlying surface, for example, the first and the second polymer layers, thus forming optical features on the surface of the substrate. Based on the design of the patterns, this enables manipulation of the light on the substrate surface during downstream sequencing imaging process.

In some embodiments, the first and the second photonic crystal material both comprise $Ta_2O_5$. In some embodiments, the patterns in the first patterned polymer layer and the second patterned polymer layers comprise micro-scale or nano-scale channels, trenches, posts, wells, or combinations thereof.

Figure 2:
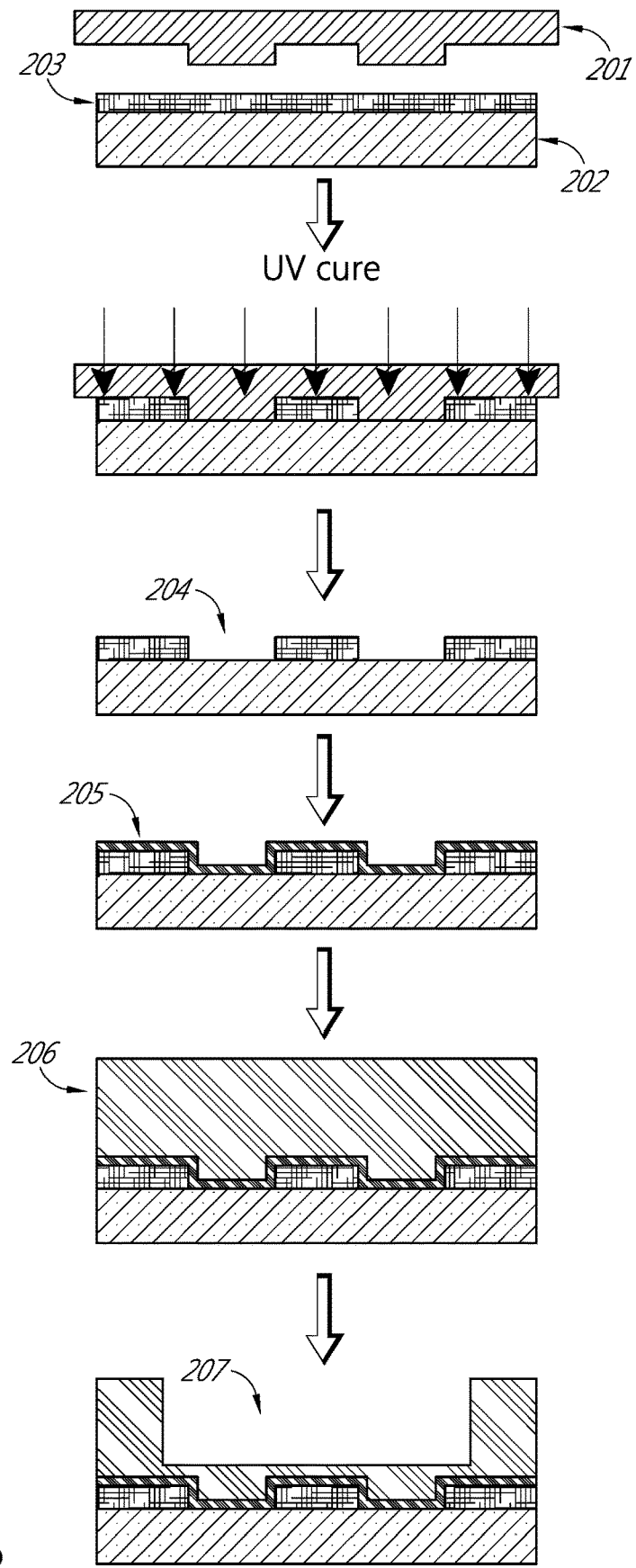
FIG. 2 illustrates an embodiment of the workflow process of preparing a dual polymer layer substrate containing photonic crystal material using nano-imprinting lithography.

FIG. 2 illustrates an embodiment of the workflow process of preparing a substrate containing photonic crystal material using nano-imprinting lithography. First, a layer of a first photocurable polymer composition 203 is deposited on the surface of a substrate 202, and a stamp 201 is imprinted on the photocurable polymer composition 203. After UV curing, a polymer layer with nanopattern 204 is formed. Then, a thin coating of a photonic crystal material 205 is sputtered on the surface of the polymer layer. Subsequently, a layer of a second photocurable polymer composition 206 is deposited on top of the photonic crystal 205, and subjected to the same nanoimprint process as described above to form a second polymer layer with nanopattern 207.

Some embodiments described herein are directed to a substrate prepared by the any of the methods described herein.

Substrate Materials

In some embodiments, substrates used in the present application include silica-based substrates, such as glass, fused silica and other silica-containing materials. In some embodiments, silica-based substrates can also be silicon, silicon dioxide, silicon nitride, silicone hydrides. In some embodiments, substrates used in the present application include plastic materials such as polyethylene, polystyrene, poly(vinyl chloride), polypropylene, nylons, polyesters, polycarbonates and poly(methyl methacrylate). Preferred plastics materials are poly(methyl methacrylate), polystyrene and cyclic olefin polymer substrates. In some embodiments, the substrate is a silica-based material or plastic material. In one embodiment, the substrate has at least one surface comprising glass.

In some other embodiments, the substrates can be a metal. In some such embodiments, the metal is gold. In some embodiments, the substrate has at least one surface comprising a metal oxide. In one embodiment, the surface comprises a tantalum oxide or titanium oxide.

Acrylamide, enone, or acrylate may also be utilized as a substrate material. Other substrate materials can include, but are not limited to gallium aresnide, indium phosphide, aluminum, ceramics, polyimide, quartz, resins, aryl azide, polymers and copolymers. The foregoing lists are intended to be illustrative of, but not limited to the present application.

In some embodiments, the substrate and/or the substrate surface can be quartz. In some other embodiments, the substrate and/or the substrate surface can be semiconductor, i.e. GaAs or ITO.

Substrates can comprise a single material or a plurality of different materials. Substrates can be composites or laminates. Substrate can be flat, round, textured and patterned. Patterns can be formed, for example, by metal pads that form features on non-metallic surfaces, for example, as described in U.S. patent application Ser. No. 13/661,524, which is incorporated herein by reference. Another useful patterned surface is one having well features formed on a surface, for example, as described in U.S. Ser. No. 13/787,396, US Pat. App. Pub. No. 2011/0172118 A1 or U.S. Pat. No. 7,622,294, each of which is incorporated herein by reference. For embodiments that use a patterned substrate, a gel can be selectively attached to the pattern features (e.g. gel can be attached to metal pads or gel can be attached to the interior of wells) or alternatively the gel can be uniformly attached across both the pattern features and the interstitial regions.

Advantages in using plastics-based substrates in the preparation and use of molecular arrays include cost: the preparation of appropriate plastics-based substrates by, for example injection-molding, is generally less expensive than the preparation, e.g. by etching and bonding, of silica-based substrates. Another advantage is the nearly limitless variety of plastics allowing fine-tuning of the optical properties of the support to suit the application for which it is intended or to which it may be put.

Where metals are used as substrates or as features on a substrate, this may be because of the desired application: the conductivity of metals can allow modulation of the electric field in DNA-based sensors. In this way, DNA mismatch discrimination may be enhanced, the orientation of immobilized oligonucleotide molecules can be affected, or DNA hybridization kinetics can be accelerated.

The substrate may be silica-based. In addition, the form and shape of the substrate employed may be varied in accordance with the application for which the present application is practiced. Generally, however, slides of support material, such as silica, e.g. fused silica, are of particular utility in the preparation and subsequent integration of molecules. Of particular use in the practice of the present application are fused silica slides sold under the trade name SPECTRASIL™. This notwithstanding, it will be evident to the skilled person that the present application is equally applicable to other presentations of substrate (including silica-based supports), such as beads, rods and the like.

In some embodiments, the surface of the substrate comprises both functional molecule-coated regions and inert regions with no coatings. In some such embodiments, the functionalized molecule coatings are hydrogel or polymer coatings. The functional molecules-coated regions can comprise reactive sites, and thus, can be used to attach molecules through chemical bonding or other molecular interactions. In some embodiments, the functional molecule-coated regions (e.g. reactive features, pads, beads or wells) and the inert regions (e.g. interstitial regions) can alternate so as to form a pattern or a grid. Such patterns can be in one or two dimensions. In some embodiments, the inert regions can be selected from glass regions, metal regions, mask regions or interstitial regions. Alternatively these materials can form reactive regions. Inertness or reactivity will depend on the chemistry and processes used on the substrate. In one embodiment, the surface comprises glass regions. In another embodiment, the surface comprises metal regions. In still another embodiment, the surface comprises mask regions. In some embodiments of the compositions described herein, the substrate can be a bead. Non-limiting exemplary substrate materials that can be coated with a polymer of the present disclosure or that can otherwise be used in a composition or method set forth herein are described in U.S. Ser. Nos. 13/492,661 and 13/661,524, each of which is incorporated herein by reference.

In some embodiments, a substrate described herein forms at least part of a flow cell or is located in a flow cell. In some such embodiments, the flow cells further comprise polynucleotides attached to the surface of the substrate via the functional molecule coating, for example, a polymer coating. In some embodiments, the polynucleotides are present in the flow cells in polynucleotide clusters, wherein the polynucleotides of the polynucleotide clusters are attached to a surface of the flow cell via the polymer coating. In such embodiments, the surface of the flow cell body to which the polynucleotides are attached is considered the substrate. In other embodiments, a separate substrate having a polymer coated surface is inserted into the body of the flow cell. In preferred embodiments, the flow cell is a flow chamber that is divided into a plurality of lanes or a plurality of sectors, wherein one or more of the plurality of lanes or plurality of sectors comprises a surface that is coated with a covalently attached polymer coating described herein. In some embodiments of the flow cells described herein, the attached polynucleotides within a single polynucleotide cluster have the same or similar nucleotide sequence. In some embodiments of the flow cells described herein, the attached polynucleotides of different polynucleotide clusters have different or nonsimilar nucleotide sequences. Exemplary flow cells and substrates for manufacture of flow cells that can be used in method or composition set forth herein include, but are not limited to, those commercially available from Illumina, Inc. (San Diego, CA) or described in U.S. Pub. Nos. 2010/0111768 A1, 2011/0059865 A1, 2012/0270305, 2014/0079923 A1, or 2015/0005447 A1, each of which is incorporated herein by reference.

In some embodiments, the substrates used in the present application are silica-based substrates. In general, silica-based substrate surface is chemically modified in some way so as to attach covalently a chemically reactive group capable of reacting with the functionalized molecules, for example, hydrogel, polymer or a partially formed hydrogel (e.g. a prepolymer (PRP)). The surface-activating agent is typically an organosilane compound. In one embodiment, the surface-activating agent is γ-methacryloxypropyltrimethoxysilane, known as "Bind Silane" or "Crosslink Silane" and commercially available from Pharmacia, although other silicon-based surface-activating agents are also known, such as monoethoxydimethylsilylbutanal, 3-mercaptopropyl-trimethoxysilane and 3-aminopropyltrimethoxysilane (all available from Aldrich). In this way, pendant functional groups such as amino groups, aldehydro groups or polymerizable groups (e.g. olefins) may be attached to the silica.

In any embodiments described herein, the substrate may be selected from a glass substrate, a silica substrate, a quartz substrate, a plastic substrate, a metal substrate, a metal oxide substrate, or combinations thereof. In some embodiments, the substrate is a glass substrate. In one embodiment, the substrate is part of a flow cell.

Analytical Applications

Some embodiments are directed to methods of detecting an analyte using a substrate described herein. In some embodiments, the analyte is selected from nucleic acid, polynucleotides, proteins, antibodies, epitopes to antibodies, enzymes, or small molecule drugs. In one embodiment, the analyte is a polynucleotide. In one embodiment, the detecting includes determining a nucleotide sequence of the polynucleotide.

Substrates of the present disclosure that contain nucleic acid arrays can be used for any of a variety of purposes. A particularly desirable use for the nucleic acids is to serve as capture probes that hybridize to target nucleic acids having complementary sequences. The target nucleic acids once hybridized to the capture probes can be detected, for example, via a label recruited to the capture probe. Methods for detection of target nucleic acids via hybridization to capture probes are known in the art and include, for example, those described in U.S. Pat. No. 7,582,420; 6,890,741; 6,913,884 or 6,355,431 or U.S. Pat. Pub. Nos. 2005/0053980 A1; 2009/0186349 A1 or 2005/0181440 A1, each of which is incorporated herein by reference. For example, a label can be recruited to a capture probe by virtue of hybridization of the capture probe to a target probe that bears the label. In another example, a label can be recruited to a capture probe by hybridizing a target probe to the capture probe such that the capture probe can be extended by ligation to a labeled oligonucleotide (e.g. via ligase activity) or by addition of a labeled nucleotide (e.g. via polymerase activity).

Some embodiments that use nucleic acids can include a step of amplifying the nucleic acids on the substrate. Many different DNA amplification techniques can be used in conjunction with the substrates described herein. Exemplary techniques that can be used include, but are not limited to, polymerase chain reaction (PCR), rolling circle amplification (RCA), multiple displacement amplification (MDA), or random prime amplification (RPA). In particular embodiments, one or more primers used for amplification can be attached to a substrate (e.g. via a polymer coating). In PCR embodiments, one or both of the primers used for amplification can be attached to the substrate. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference.

PCR amplification can also be carried out with one of the amplification primers attached to a substrate and the second primer in solution. An exemplary format that uses a combination of one attached primer and soluble primer is emulsion PCR as described, for example, in Dressman et al., *Proc. Natl. Acad. Sci. USA* 100:8817-8822 (2003), WO 05/010145, or U.S. Patent Publ. Nos. 2005/0130173 or 2005/0064460, each of which is incorporated herein by reference. Emulsion PCR is illustrative of the format and it will be understood that for purposes of the methods set forth herein the use of an emulsion is optional and indeed for several embodiments an emulsion is not used. Furthermore, primers need not be attached directly to substrate or solid supports as set forth in the ePCR references and can instead be attached to a polymer coating as set forth herein.

RCA techniques can be modified for use in a method of the present disclosure. Exemplary components that can be used in an RCA reaction and principles by which RCA produces amplicons are described, for example, in Lizardi et al., *Nat. Genet.* 19:225-232 (1998) and US 2007/0099208 A1, each of which is incorporated herein by reference. Primers used for RCA can be in solution or attached to a polymer coating.

MDA techniques can be modified for use in a method of the present disclosure. Some basic principles and useful conditions for MDA are described, for example, in Dean et al., *Proc Natl. Acad. Sci. USA* 99:5261-66 (2002); Lage et al., *Genome Research* 13:294-307 (2003); Walker et al., Molecular Methods for Virus Detection, Academic Press, Inc., 1995; Walker et al., Nucl. Acids Res. 20:1691-96 (1992); U.S. Pat. Nos. 5,455,166; 5,130,238; and 6,214,587, each of which is incorporated herein by reference. Primers used for MDA can be in solution or attached to a polymer coating.

In particular embodiments a combination of the above-exemplified amplification techniques can be used. For example, RCA and MDA can be used in a combination wherein RCA is used to generate a concatameric amplicon in solution (e.g. using solution-phase primers). The amplicon can then be used as a template for MDA using primers that are attached to a substrate (e.g. via a polymer coating). In this example, amplicons produced after the combined RCA and MDA steps will be attached to the substrate.

In some embodiments, a substrate described herein can be used for determining a nucleotide sequence of a polynucleotide. In such embodiments, the method can comprise the steps of (a) contacting a polynucleotide polymerase with polynucleotide clusters attached to a surface of a substrate (e.g. via any one of the polymer or hydrogel coatings described herein); (b) providing nucleotides to the surface of the substrate such that a detectable signal is generated when one or more nucleotides are utilized by the polynucleotide polymerase; (c) detecting signals at one or more attached polynucleotide (or one or more clusters produced from the attached polynucleotides); and (d) repeating steps (b) and (c), thereby determining a nucleotide sequence of a substrate-attached polynucleotide.

Nucleic acid sequencing can be used to determine a nucleotide sequence of a polynucleotide by various processes known in the art. In a preferred method, sequencing-by-synthesis (SBS) is utilized to determine a nucleotide sequence of a polynucleotide attached to a surface of a substrate (e.g. via any one of the polymer coatings described herein). In such process, one or more nucleotides are provided to a template polynucleotide that is associated with a polynucleotide polymerase. The polynucleotide polymerase incorporates the one or more nucleotides into a newly synthesized nucleic acid strand that is complementary to the polynucleotide template. The synthesis is initiated from an oligonucleotide primer that is complementary to a portion of the template polynucleotide or to a portion of a universal or non-variable nucleic acid that is covalently bound at one end of the template polynucleotide. As nucleotides are incorporated against the template polynucleotide, a detectable signal is generated that allows for the determination of which nucleotide has been incorporated during each step of the sequencing process. In this way, the sequence of a nucleic acid complementary to at least a portion of the template polynucleotide can be generated, thereby permitting determination of the nucleotide sequence of at least a portion of the template polynucleotide. Flow cells provide a convenient format for housing an array that is produced by the methods of the present disclosure and that is subjected to a sequencing-by-synthesis (SBS) or other detection technique that involves repeated delivery of reagents in cycles. For example, to initiate a first SBS cycle, one or more labeled nucleotides, DNA polymerase, etc., can be flowed into/through a flow cell that houses a nucleic acid array made by methods set forth herein. Those sites of an array where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., Nature 456: 53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference in its entirety.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568 and 6,274,320, each of which is incorporated herein by reference in its entirety). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to arrays of the present disclosure are described, for example, in WO 12/058096 A1, US 2005/0191698 A1, U.S. Pat. Nos. 7,595,883, and 7,244,559, each of which is incorporated herein by reference in its entirety.

Sequencing-by-ligation reactions are also useful including, for example, those described in Shendure et al. Science 309:1728-1732 (2005); U.S. Pat. Nos. 5,599,675; and 5,750,341, each of which is incorporated herein by reference in its entirety. Some embodiments can include sequencing-by-hybridization procedures as described, for example, in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which is incorporated herein by reference in its entirety. In both sequencing-by-ligation and sequencing-by-hybridization procedures, nucleic acids that are present at sites of an array are subjected to repeated cycles of oligonucleotide delivery and detection. Fluidic systems for SBS methods as set forth herein or in references cited herein can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al. Science 299, 682-686 (2003); Lundquist et al. Opt. Lett. 33, 1026-1028

(2008); Korlach et al. *Proc. Natl. Acad. Sci. USA* 105, 1176-1181 (2008), the disclosures of which are incorporated herein by reference in its entirety.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in US 2009/0026082 A1; US 2009/0127589 A1; US 2010/0137143 A1; or US 2010/0282617 A1, each of which is incorporated herein by reference in its entirety.

Another useful application for a device of the present disclosure is, for example, part of gene expression analysis. Gene expression can be detected or quantified using RNA sequencing techniques, such as those, referred to as digital RNA sequencing. RNA sequencing techniques can be carried out using sequencing methodologies known in the art such as those set forth above. Gene expression can also be detected or quantified using hybridization techniques carried out by direct hybridization to a substrate or using a multiplex assay, the products of which are detected on a substrate. A substrate of the present disclosure, for example, having been produced by a method set forth herein, can also be used to determine genotypes for a genomic DNA sample from one or more individual. Exemplary methods for gene array-based expression and genotyping analysis that can be carried out on an array of the present disclosure are described in U.S. Pat. No. 7,582,420; 6,890,741; 6,913,884 or 6,355,431 or US Pat. Pub. Nos. 2005/0053980 A1; 2009/0186349 A1 or US 2005/0181440 A1, each of which is incorporated herein by reference in its entirety.

In some embodiments of the above-described method, which employ a flow cell, only a single type of nucleotide is present in the flow cell during a single flow step. In such embodiments, the nucleotide can be selected from the group consisting of dATP, dCTP, dGTP, dTTP and analogs thereof. In other embodiments of the above-described method which employ a flow cell, a plurality different types of nucleotides are present in the flow cell during a single flow step. In such methods, the nucleotides can be selected from dATP, dCTP, dGTP, dTTP and analogs thereof.

Determination of the nucleotide or nucleotides incorporated during each flow step for one or more of the polynucleotides attached to the polymer coating on the surface of the substrate present in the flow cell is achieved by detecting a signal produced at or near the polynucleotide template. In some embodiments of the above-described methods, the detectable signal comprises and optical signal. In other embodiments, the detectable signal comprises a non-optical signal. In such embodiments, the non-optical signal comprises a change in pH at or near one or more of the polynucleotide templates.

Applications and uses of substrates of the present disclosure have been exemplified herein with regard to nucleic acids. However, it will be understood that other analytes can be attached to a substrate set forth herein and analyzed. One or more analytes can be present in or on a substrate of the present disclosure. The substrates of the present disclosure are particularly useful for detection of analytes, or for carrying out synthetic reactions with analytes. Thus, any of a variety of analytes that are to be detected, characterized, modified, synthesized, or the like can be present in or on a substrate set forth herein. Exemplary analytes include, but are not limited to, nucleic acids (e.g. DNA, RNA or analogs thereof), proteins, polysaccharides, cells, antibodies, epitopes, receptors, ligands, enzymes (e.g. kinases, phosphatases or polymerases), small molecule drug candidates, or the like. A substrate can include multiple different species from a library of analytes. For example, the species can be different antibodies from an antibody library, nucleic acids having different sequences from a library of nucleic acids, proteins having different structure and/or function from a library of proteins, drug candidates from a combinatorial library of small molecules etc.

In some embodiments, analytes can be distributed to features on a substrate such that they are individually resolvable. For example, a single molecule of each analyte can be present at each feature. Alternatively, analytes can be present as colonies or populations such that individual molecules are not necessarily resolved. The colonies or populations can be homogenous with respect to containing only a single species of analyte (albeit in multiple copies). Taking nucleic acids as an example, each feature on a substrate can include a colony or population of nucleic acids and every nucleic acid in the colony or population can have the same nucleotide sequence (either single stranded or double stranded). Such colonies can be created by cluster amplification or bridge amplification as set forth previously herein. Multiple repeats of a target sequence can be present in a single nucleic acid molecule, such as a concatamer created using a rolling circle amplification procedure. Thus, a feature on a substrate can contain multiple copies of a single species of an analyte. Alternatively, a colony or population of analytes that are at a feature can include two or more different species. For example, one or more wells on a substrate can each contain a mixed colony having two or more different nucleic acid species (i.e. nucleic acid molecules with different sequences). The two or more nucleic acid species in a mixed colony can be present in non-negligible amounts, for example, allowing more than one nucleic acid to be detected in the mixed colony.

Polynucleotides Arrays and Sequencing Application

Other embodiments of the methods described herein relate to preparing an array of polynucleotides using a substrate described herein. In such embodiments, the methods can comprise the steps of covalently attaching a plurality of oligonucleotides to the reactive sites present in the first polymer layer (i.e., first plurality of functional groups) on the substrate surface, either directly or indirectly through reaction with an intermediate coating attached to the first polymer layer; contacting the plurality of oligonucleotides attached to the substrate with templates to be amplified, each template comprising a sequence capable of hybridizing to the oligonucleotides; and amplifying the templates using the oligonucleotides, thereby generating a clustered array of polynucleotides. For example, tetrazine terminated primers can react with norbornene moieties of the substrate surface to form covalent bonding, BCN-terminated primers can react with the azido moieties of the substrate surface, and triazolinedione terminated primers can react with diene or indole moieties of the substrate surface. See, for example, Billiet et al., *Nature Chemistry* 6, 815-821 (2014).

In some embodiments two primers can be used, one or both of which can be attached to the polymer coating. For example, the methods can comprise the steps of reacting a plurality of first oligonucleotides with the first polymer layer on the substrate surface as described herein; contacting the plurality of first oligonucleotides attached to the substrate with templates to be amplified, each template comprising at the 3' end a sequence capable of hybridizing to the first oligonucleotides and at the 5' end a sequence the complement of which is capable of hybridizing to a second oligonucleotides; and amplifying the templates using the first oligonucleotides and the second oligonucleotides, wherein the second oligonucleotide is optionally attached to the substrate, thereby generating a clustered array of polynucleotides.

Some embodiments of the compositions described herein relate to a flow cell comprising a substrate described herein. Some such embodiments further comprise polynucleotides attached to the surface of the substrate. In some embodiments, the polynucleotides are present in polynucleotide clusters. In some such embodiments, polynucleotides within a single polynucleotide cluster have the same nucleotide sequence. Individual polynucleotides in a cluster can be attached to the substrate at one end or at both ends. The attachment(s) can be via the 5' and/or 3' end of a strand of the polynucleotide. Polynucleotides of different polynucleotide clusters generally have different nucleotide sequences, but this is not necessary in all embodiments.

Some embodiments of the methods described herein relate to determining a nucleotide sequence of a polynucleotide. Some such embodiments comprise the steps of: (a) contacting a polynucleotide polymerase with polynucleotide clusters attached to a surface of the substrate as described herein; (b) providing nucleotides to the surface of the substrate such that a detectable signal is generated when one or more nucleotides are utilized by the polynucleotide polymerase; (c) detecting signals at one or more polynucleotide clusters; and (d) repeating steps (b) and (c), thereby determining a nucleotide sequence of a polynucleotide present at the one or more polynucleotide clusters. In some such embodiments, the surface of the substrate is present within a flow cell. In some such embodiments, only a single type of nucleotide is present in the flow cell during a single flow step. In such embodiments, the nucleotide can be selected from dATP, dCTP, dGTP, dTTP and analogs thereof. In other embodiments of the methods of determining a nucleotide sequence of a polynucleotide, a plurality different types of nucleotides are present in the flow cell during a single flow step. In such embodiments, the nucleotides can be selected from dATP, dCTP, dGTP, dTTP and analogs thereof. In further embodiments of the methods of determining a nucleotide sequence of a polynucleotide, the detectable signal comprises and optical signal. In other embodiments, the detectable signal comprises a non-optical signal. In such embodiments, the non-optical signal can be a change in pH or a change in concentration of pyrophosphate.

What is claimed is:

1. A system, comprising:
   a substrate having a surface;
   a first polymer layer disposed on the substrate surface, wherein the first polymer layer comprises a first plurality of functional groups and further comprises an imprinted pattern of features; and
   a second polymer layer disposed over at least a portion of the first polymer layer;
      wherein the first plurality of functional groups provide reactive sites for covalent bonding of a functionalized molecule and the second polymer layer comprises a second plurality of functional groups that differ from the first plurality of functional groups;
      wherein a first region of the system is defined where the first polymer layer is exposed; and
      wherein a second region of the system is defined where the second polymer layer is exposed.

2. The system of claim 1, wherein the first and the second polymer layers do not comprise silicon or silicon oxide.

3. The system of claim 1, wherein the imprinted pattern of features comprises micro-scale or nano-scale patterns; and wherein the micro-scale or nano-scale patterns comprise channels, trenches, posts, wells, or combinations thereof.

4. The system of claim 1, wherein the second region is not patterned.

5. The system of claim 1, wherein the first region and the second region have opposite character with regard to hydrophobicity and hydrophilicity.

6. The system of claim 1, wherein a thickness of the first polymer layer is greater than a thickness of the second polymer layer.

7. The system of claim 1, wherein the first plurality of functional groups of the first polymer layer is selected from the group consisting of $C_{8-14}$ cycloalkenes, 8 to 14 membered heterocycloalkenes, $C_{8-14}$ cycloalkynes, 8 to 14 membered heterocycloalkynes, alkynyl, vinyl, halo, azido, amino, amido, epoxy, glycidyl, carboxyl, hydrazonyl, hydrazinyl, hydroxy, tetrazolyl, tetrazinyl, nitrile oxide, nitrene, nitrone, thiol, and optionally substituted variants and combinations thereof.

8. The system of claim 1, wherein the first plurality of functional groups of the first polymer layer is selected from the group consisting of halo, azido, alkynyl, carboxyl, epoxy, glycidyl, norbornene, amino, and optionally substituted variants and combinations thereof.

9. The system of claim 1, further comprising a functionalized molecule, the functionalized molecule comprising a polymer, a hydrogel, an amino acid, a peptide, a nucleoside, a nucleotide, a polynucleotide, a sugar, a protein, or combinations thereof covalently attached to the first polymer layer through reaction with the first plurality of functional groups.

10. The system of claim 9, wherein the functionalized molecule comprises poly(N-(5-azidoacetamidylpentyl)acrylamide-co-acrylamide) (PAZAM).

11. The system of claim 10, wherein the functionalized molecule further comprises oligonucleotides covalently bonded to PAZAM.

12. The system of claim 1, wherein the substrate is selected from the group consisting of a glass substrate, a silica substrate, a quartz substrate, a plastic substrate, a metal substrate, a metal oxide substrate, and combinations thereof.

13. The system of claim 1, wherein the substrate is a glass substrate.

* * * * *

```
                        SEQUENCE LISTING

<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: primer_bind

<400> SEQUENCE: 1
aatgatacgg cgaccaccga gauctacac                                        29

<210> SEQ ID NO 2
<211> LENGTH: 24
<212> TYPE: DNA
<213> ORGANISM: Artificial Sequence
<220> FEATURE:
<223> OTHER INFORMATION: primer_bind

<400> SEQUENCE: 2
caagcagaag acggcatacg agat                                             24

<210> SEQ ID NO 3
<211> LENGTH: 20
<212> TYPE: DNA
<213> ORGANISM: Artificial Sequence
<220> FEATURE:
<223> OTHER INFORMATION: primer_bind

<400> SEQUENCE: 3
aatgatacgg cgaccaccga                                                  20

<210> SEQ ID NO 4
<211> LENGTH: 21
<212> TYPE: DNA
<213> ORGANISM: Artificial Sequence
<220> FEATURE:
<223> OTHER INFORMATION: primer_bind

<400> SEQUENCE: 4
caagcagaag acggcatacg a                                                21
```